United States Patent
Reimer et al.

(10) Patent No.: US 7,839,494 B2
(45) Date of Patent: Nov. 23, 2010

(54) OPHTHALMIC SURGICAL MICROSCOPE HAVING AN OCT-SYSTEM

(75) Inventors: Peter Reimer, Ellwangen (DE); Christoph Hauger, Aalen (DE); Alfons Abele, Schwäbisch Gmünd (DE); Markus Seesselberg, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 286 days.

(21) Appl. No.: 11/984,819

(22) Filed: Nov. 21, 2007

(65) Prior Publication Data

US 2008/0117432 A1 May 22, 2008

(30) Foreign Application Priority Data

Nov. 6, 2006 (DE) ........................ 10 2006 052 513
Apr. 24, 2007 (DE) ........................ 10 2007 019 680

(51) Int. Cl.
*G01N 21/00* (2006.01)
*G01B 9/02* (2006.01)

(52) U.S. Cl. ........................................ 356/73; 356/497

(58) Field of Classification Search ................. 356/479, 356/497, 72
See application file for complete search history.

(56) References Cited

U.S. PATENT DOCUMENTS 5,321,501 A 6/1994 Swanson et al.
5,493,109 A 2/1996 Wei et al.
6,004,314 A 12/1999 Wei et al.

FOREIGN PATENT DOCUMENTS

| DE | 94 15 219 U1 | 1/1995 |
| DE | 10 2004 049 368 | 4/2006 |
| EP | 0 815 801 | 1/1998 |
| EP | 1 326 117 | 7/2003 |
| WO | WO 2006/100544 | 9/2006 |

OTHER PUBLICATIONS

Expanded European Search Report (Translation into English).

*Primary Examiner*—Hwa S. A Lee
(74) *Attorney, Agent, or Firm*—Walter Ottesen

(57) ABSTRACT

An ophthalmic surgical microscope (100) has a microscope main objective (101) and a viewing beam path (105) which passes through the microscope main objective (101) for visualizing an object region. The ophthalmic surgical microscope (100) includes an OCT-system (140) for recording images of the object region (108). The OCT-system (140) includes an OCT-scanning beam (142) which is guided via a scan mirror arrangement (146) to the object region (108). An optic element (147) is provided between the scan mirror arrangement (146) and the microscope main objective (101). This optic element (147) bundles the OCT-scanning radiation exiting from the scan mirror arrangement (146) and transfers the same into a beam path which passes through the microscope main objective (101). Alternatively or in addition, the ophthalmic surgical microscope (100) includes an opthalmoscopic magnifier lens (132) which can be pivoted into and out of the viewing beam path (105) and the OCT-scanning beam (142).

18 Claims, 6 Drawing Sheets

OPHTHALMIC SURGICAL MICROSCOPE HAVING AN OCT-SYSTEM

CROSS REFERENCE TO RELATED APPLICATION

This application claims priority of German patent application no. 10 2007 019 680.8, filed Apr. 24, 2007, the entire which are content of which is incorporated herein by reference.

FIELD OF THE INVENTION

The invention relates to an ophthalmic surgical microscope having a microscope main objective and a viewing beam path which passes through the microscope main objective. The ophthalmic surgical microscope further includes an OCT-system for recording images of an object region. The OCT-system includes an OCT-scanning beam which is guided via a scan mirror unit to the object region.

BACKGROUND OF THE INVENTION

A surgical microscope of the kind referred to above is known from U.S. Pat. No. 6,004,314. This surgical microscope includes an OCT-system which generates a scanning beam of short coherent laser radiation. The OCT-system includes an analyzer unit for evaluating interference signals. The OCT-system further includes a device having two scan mirrors for scanning the OCT-scanning beam. These scan mirrors can be displaced about two axes of movement. The OCT-scanning beam in the surgical microscope is coupled via a divider mirror into the illuminating beam path of the surgical microscope. The OCT-scanning beam is deflected with the illuminating beam through the microscope main objective to the object region.

Via optical coherence tomography, an OCT-system makes possible the non-invasive display and measurement of structures within a tissue. As an optical image producing method, the optical coherence tomography especially generates section and volume images of biological tissue with a micrometer resolution. A corresponding OCT-system includes a source for time-dependent incoherent and spatially coherent light having a specific coherence length which is guided to a specimen beam path and a reference beam path. The specimen beam path is directed to the tissue to be examined. Laser radiation, which is backscattered into the specimen beam path because of scatter centers in the tissue, superposes the OCT-system with laser radiation from the reference beam path. An interference signal results because of the superposition. The positions of the scattering centers for the laser radiation in the examined tissue are determined from this interference signal.

For OCT-systems, the building principles of the "time-domain OCT" and of the "Fourier-domain OCT" are known.

The configuration of a "time-domain OCT" is described, for example, in U.S. Pat. No. 5,321,501 with reference to FIG. 1a at column 5, line 40, to column 11, line 10. In a system of this kind, the optical path length of the reference beam path is continuously varied via a rapidly moving reference mirror. The light from specimen beam path and reference beam path is superposed on a photo detector. When the optical path lengths of the specimen and reference beam paths are coincident, an interference signal is provided on the photo detector.

A "Fourier-domain OCT" is, for example, described in international patent publication WO 2006/100544 A1. To measure the optical path length of a specimen beam path, light from the specimen beam path is superposed onto light from a reference beam path. In contrast to the time-domain OCT, the light from the specimen beam path and reference beam path is not supplied directly to a detector for a measurement of the optical path length of the specimen beam path but is first spectrally dispersed by means of a spectrometer. The spectral intensity of the superposed signal generated in this manner from specimen beam path and reference beam path is then detected by a detector. By evaluating the detector signal, the optical path length of the specimen beam path can be determined.

SUMMARY OF THE INVENTION

It is an object of the invention to provide a compactly configured ophthalmic surgical microscope which permits the recordation of OCT-section images of the human eye. Here, the OCT-scanning beam can be guided to an OCT-scanning plane without intensity losses.

The ophthalmic surgical microscope of the invention is for defining a viewing beam path and includes: a microscope main objective mounted so as to permit the viewing beam path to pass therethrough permitting examination of a region of an object; an OCT-system for recording images of the object region; the OCT-system providing an OCT-scanning beam and including a scanning mirror device for scanning the OCT-scanning beam; and, an optical unit mounted between the scanning mirror device and the microscope main objective for bundling the OCT-scanning beam exiting from the scanning mirror device and guiding the bundled OCT-scanning beam into a beam path passing through the microscope main objective to the object region.

In another embodiment of the invention, the ophthalmic surgical microscope is for defining a viewing beam path and includes: a microscope main objective mounted so as to permit the viewing beam path to pass therethrough permitting examination of a region of an object; an OCT-system for recording images of the object region; the OCT-system providing an OCT-scanning beam and including a scanning mirror device for scanning the OCT-scanning beam; an ophthalmoscopic magnifier lens being movably mounted; the ophthalmoscopic magnifier lens being movable between a first position whereat the viewing beam path and the OCT-scanning beam path pass through the ophthalmoscopic magnifier lens and a second position whereat the viewing beam path and the OCT-scanning beam path do not pass through the ophthalmoscopic magnifier lens.

The ophthalmoscopic magnifier lens permits bundling the OCT-scanning beam on the ocular fundus of the patient in order to scan the ocular fundus and to simultaneously make the fundus visible in the ocular via the optical viewing beam paths of the surgical microscope.

According to another feature of the invention, the optical element between the scan mirror unit and the microscope main objective is configured as a movable lens unit. In this way, different section planes of a human eye can be scanned with OCT-radiation.

According to another feature of the invention, this optical element is accommodated in a lens exchange unit. In this way, a rapid-back and forth switching between different scanning planes for OCT-radiation is possible in the object region.

According to another feature of the invention, the optical element is configured as a zoom system having variable focal length. In this way, a continuous variation of section planes examined in a patient eye is made possible with OCT-radiation.

According to another feature of the invention, means for adjusting the focal length of the main objective are provided. In this way, different planes of an object region can be examined with the ophthalmic surgical microscope without it being necessary to shift the surgical microscope.

According to another feature of the invention, the scan mirror unit for scanning the OCT-scanning beam has a first scanning mirror. Preferably, and additionally, a second scan mirror is provided. The first scan mirror can be moved about a first rotational axis and the second scan mirror can be moved about a second rotational axis. The first rotational axis and the second rotational axis are laterally offset at right angles to each other. In this way, an object can be scanned with a raster pattern running perpendicular to each other.

According to another feature of the invention, the OCT-system includes a light conductor which has a light exit section for the OCT-scanning beam. Means are assigned to the light conductor for moving the same. In this way, the OCT-system can be adapted for the use of OCT-radiation of different wavelengths.

According to another feature of the invention, an ophthalmoscopic magnifier lens is provided in the ophthalmic surgical microscope which can be pivoted into and out of the viewing beam path and the OCT-scanning beam path. Preferably, this ophthalmoscopic magnifier lens is combined with a reduction lens. The ophthalmoscopic magnifier lens and the reduction lens are arranged in an ophthalmic ancillary module which can be pivoted into and out of the OCT-scanning beam path and the viewing beam path. In this way, the anterior section of the patient eye as well as the ocular fundus can be examined with OCT-radiation with the ophthalmic surgical microscope.

According to another feature of the invention, the OCT-system in the ophthalmic surgical microscope is designed for making available a first OCT-scanning light beam at a first wavelength and for making available a second OCT-scanning light beam having a second wavelength different from the first wavelength. Preferably, a corresponding first OCT-system and a corresponding second OCT-system are provided which make available the OCT-scanning light beams of different wavelengths. In this way, body tissue having different absorption characteristics for OCT-radiation can be examined with good resolution.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
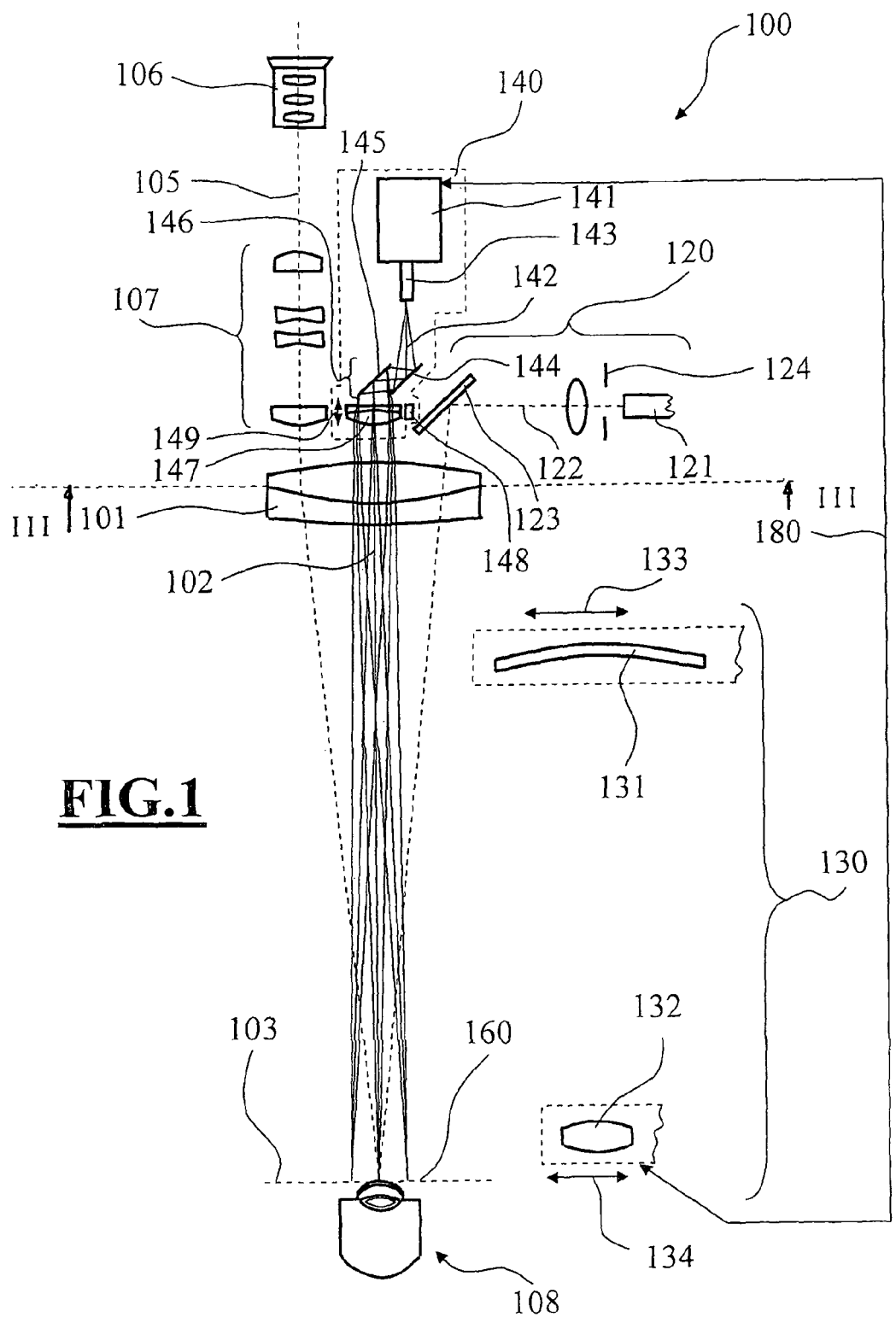
FIG. 1 is a schematic showing an ophthalmic surgical microscope having an ophthalmic ancillary module and a first OCT-system.

The surgical microscope 100 in FIG. 1 has a microscope main objective 101 defining an optical axis 102 as well as a focal plane 103. Stereoscopic viewing beam paths 105 of a binocular tube 106 pass through the microscope main objective 101.

The surgical microscope 100 has an illumination unit in the form of an illumination module 120 for illuminating the object region in the form of a patient eye 108. This illumination module 120 includes a first light conductor 121 which makes illuminating light 122 available from a light source (not shown). A displaceable field diaphragm 124 is illuminated by the illuminating light 122 exiting from the light conductor 121. A path-folding mirror 123 is mounted on the side of the microscope main objective 101 facing away from the object. The illuminating light exiting from the light conductor 121 is directed via path-folding mirror 123 through the microscope main objective 101 and into the object region 108.

An ophthalmoscopic ancillary module 130 has a reducer lens 131 and an ophthalmoscopic magnifier lens 132 which can be pivoted into and out of the stereoscopic viewing beam path 105 of the surgical microscope 100 in correspondence to double arrows (133, 134). The ophthalmoscopic ancillary module is assigned to the ophthalmic surgical microscope 100.

Figure 2:
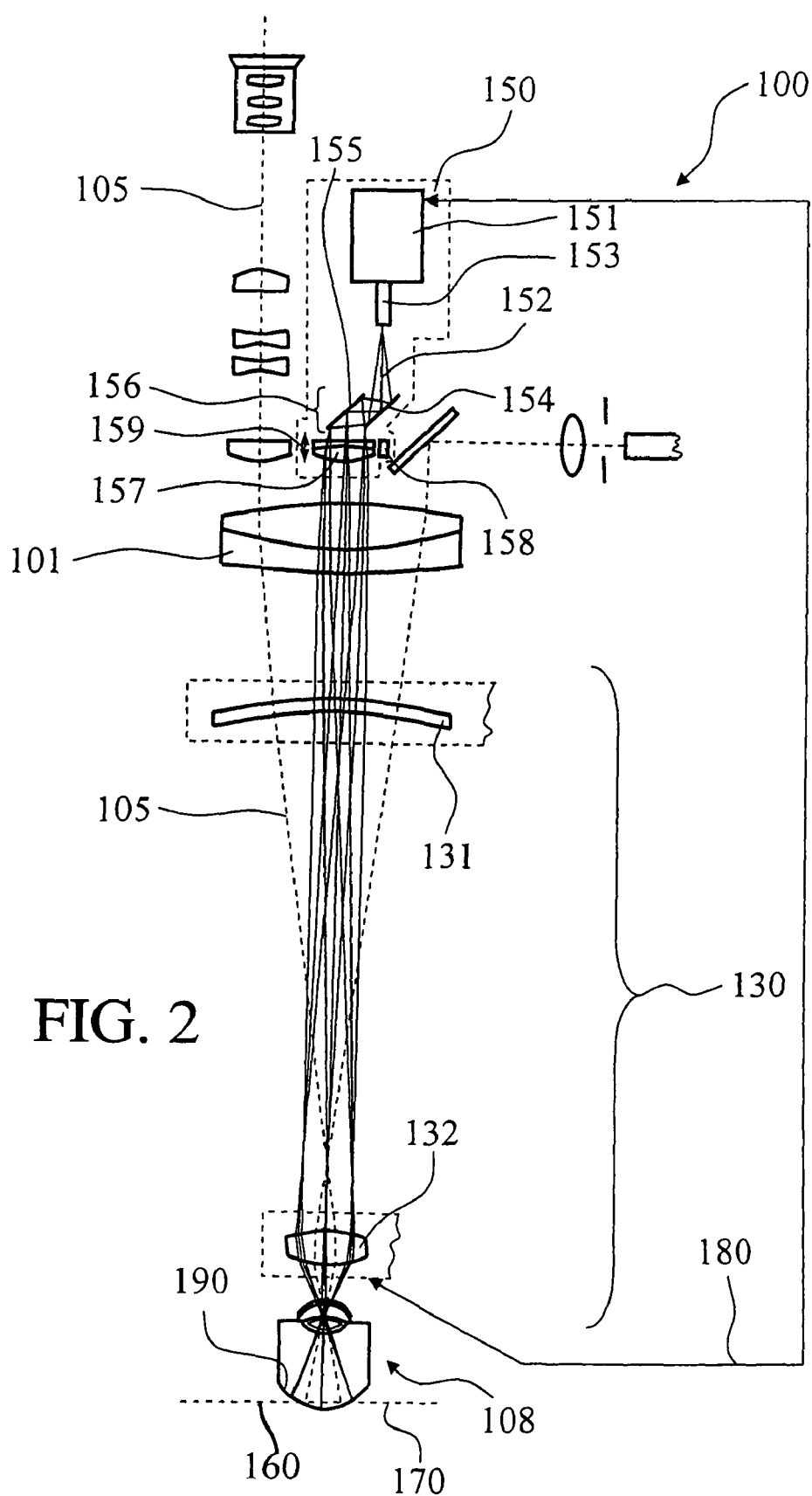
FIG. 2 shows the ophthalmic surgical microscope of FIG. 1 having a second OCT-system wherein the ophthalmic ancillary module is pivoted into the viewing beam path of the ophthalmic surgical microscope.

A first OCT-system 140 is provided in the ophthalmic surgical microscope 100. The ophthalmic surgical microscope further contains a second OCT-system 150 which is shown in FIG. 2. These OCT-systems permit the recordation of OCT-images.

The OCT-system 140 of FIG. 1 includes a unit 141 for generating and analyzing an OCT-scanning beam 142. The unit 141 is integrated into the surgical microscope 100. The unit 141 can, however, also be mounted outside of the surgical microscope 100 in a corresponding stand console. The unit 141 is connected to a light conductor 143 which makes the OCT-scanning beam 142 available.

The OCT-scanning beam 142, which exits from the light conductor 143, is guided with a divergent beam path onto a first scan mirror 144 and a second scan mirror 145 of an OCT-scan unit 146. From there, the OCT-scanning beam passes through an optic element in the form of a converging lens 147 to thereafter pass through the microscope main objective 101. The OCT-scanning beam 142 is bundled in an OCT-scanning plane 160 in the anterior section of the patient eye 108.

The OCT-light, which is backscattered from the object region in the form of a patient eye 108 into the OCT-scanning beam path, arrives back in the unit 141 via the microscope main objective 101, the converging lens 147 and the OCT-scanning unit 146. In unit 141, the OCT-scanning light, which is backscattered from the object region, interferes with the OCT-radiation from a reference beam path. The interference signal is detected by a detector and is evaluated by a computer unit which, from the signal, determines an optical path length difference between scatter centers for OCT-light in the object region and the path length of light in the reference branch.

A displacing mechanism 148 is assigned to the converging lens 147 for adjusting the OCT-scanning plane 160. The converging lens 147 can be moved by the displacing mechanism 148 in correspondence to the double arrow 149.

The first OCT-system 140 operates at a wavelength of λ=1310 nm. The second OCT-system in the ophthalmic surgical microscope 100 is configured to correspond to the first OCT-system 140 but has a work wavelength of λ=800 nm. It is understood that the OCT-systems can also be designed for other operating wavelengths. Operating wavelengths can be realized in the range 600 nm<λ<1500 nm and are advantageous depending upon application.

FIG. 2 shows the ophthalmic surgical microscope 100 of FIG. 1 with the second OCT-system 150. The second OCT-system 150 is configured and arranged in correspondence to the first OCT-system 140.

Identical component groups of the surgical microscope are provided in FIG. 2 with the same reference numerals.

The OCT-system 150 has a unit 151 for generating and analyzing an OCT-scanning beam 152 of the OCT-system 150. The OCT-system 150 generates OCT-scanning radiation 152 at the exit end of the light conductor 153. In the same manner as the OCT-scanning beam 142 of OCT-system 140 of FIG. 1, this OCT-scanning beam 152 is guided via an OCT-scanning unit 156 having a first scan mirror 154 and a second scan mirror 155 via an optical element through the microscope main objective 101. This optical element is configured as a converging lens 157.

FIG. 2 shows the ophthalmic surgical microscope 100 in an operating mode wherein the reducer lens 131 and the ophthalmoscopic magnifier lens 132 of the ophthalmic ancillary module 130 are pivoted into the viewing beam path 205 of the surgical microscope 100. This makes possible an examination of the ocular fundus 190 of the patient eye 108 with the OCT-scanning light and with light which arrives from the ocular fundus 190 back in the viewing beam paths of the surgical microscope.

The converging lens 157 bundles the OCT-scanning beam and directs this beam to the microscope main objective 101. The OCT-scanning beam reaches the patient eye 108 via the microscope main objective 101, the reducer lens 131 and the opthalmoscopic magnifier lens 132 and is bundled in the OCT-scanning plane 160 (FIG. 6) at the ocular fundus 190 of patient eye 108.

The OCT-light, which is backscattered into the OCT-scanning beam path from the object region in the form of a patient eye 108, is guided back into the unit 151 for generating and analyzing an OCT-scanning beam. The backscattered OCT-light is guided into the unit 151 via the microscope main objective 101, the converging lens 157 and the OCT-scanning unit 156. In the unit 151, the OCT-scanning light, which is backscattered from the object region, in turn interferes with OCT-radiation from a reference beam path. As in the OCT-system 140, the interference signal is detected by a detector in the OCT-system 150 and is evaluated by a computer unit which, from the signal, determines an optical path length difference between scattering centers for OCT-light in the object region and the path length of light in the reference branch.

A displacing mechanism 158 is assigned to the converging lens 157 which can be moved by the mechanism 158 in correspondence to the double arrow 159. In this way, a focal plane can be adjusted also for the OCT-scanning beam from the OCT-system 150.

The optical path length of the OCT-scanning beam path in the operating mode of the ophthalmic surgical microscope 100 shown in FIG. 2 is longer than in the operating mode of FIG. 1. This requires an adaptation of the optical path length in the reference beam path of the OCT-system 150. For this purpose, a coupling 180 of ophthalmoscopic magnifier lens 132 and OCT-system 150 is provided which effects, with a pivoting of the ophthalmoscopic magnifier lens 132 into the viewing beam path and the OCT-beam path, the optical path length of the reference beam path in the OCT-system to increase by a specific value. This value is preferably held to be adjustable. A fixed value advantageously orients itself to the average length of the patient eye.

Figure 3:
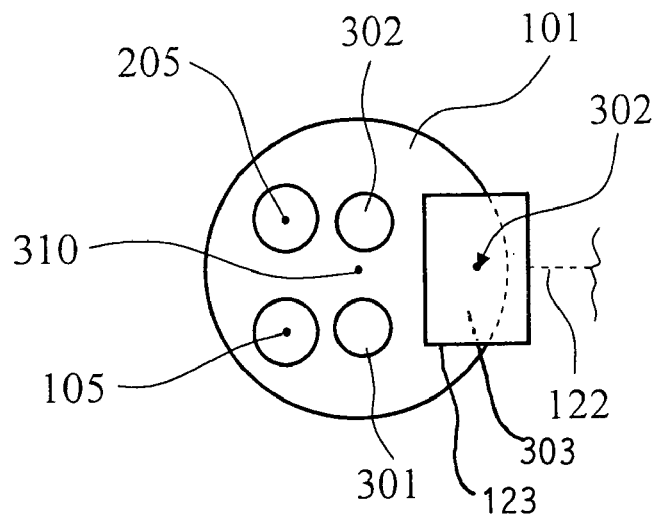
FIG. 3 is a section view of the microscope main objective taken along line III-III of FIG. 1.

FIG. 3 is a section view taken along line III-III of FIG. 1. FIG. 3 shows the course of the stereoscopic viewing beam paths (105, 205) of the surgical microscope 100 of FIG. 1. Two stereoscopic component beams (105, 205) pass through the microscope main objective 101. The optical axis 102 of the microscope main objective lies at the center 310 thereof. The OCT-scanning beam 142 of the OCT-system 140 passes through the microscope main objective 101 in the region 301. The OCT-scanning beam 152 of the OCT-system 150 of FIG. 2 passes through the microscope main objective 101 in region 302 and the illuminating light 122 passes through the objective 101 in the region 303.

Figure 4:
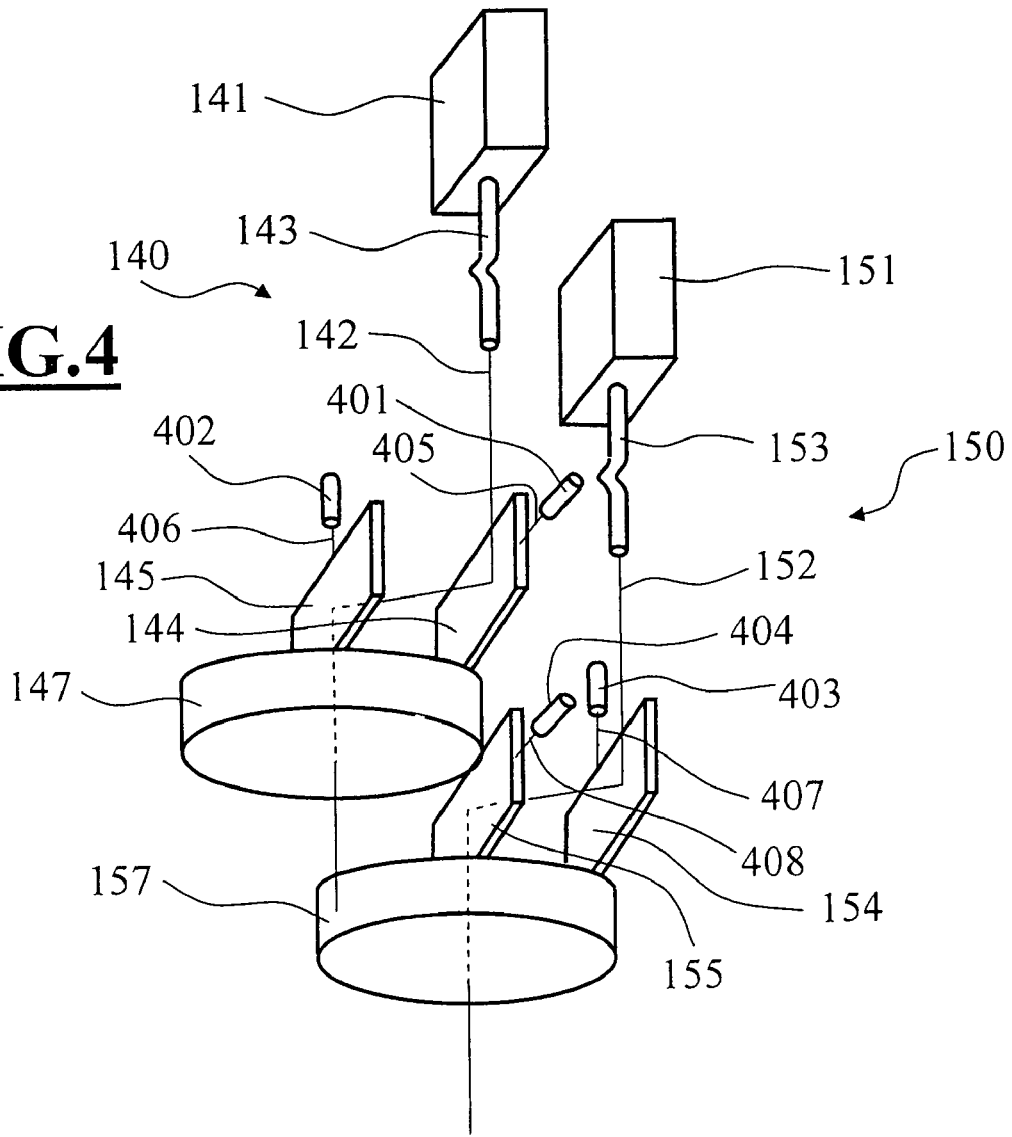
FIG. 4 is a detail view of the ophthalmic surgical microscope having first and second OCT-systems.

FIG. 4 shows the first OCT-system 140 and the second OCT-system 150 in the surgical microscope 100 of FIGS. 1 and 2. The wavelength range of the OCT-scanning beams of the two OCT-systems (140, 150) is, however, different: the first OCT-system is based on an OCT-scanning beam having the wavelength $\lambda_1$=1310 nm. The second OCT-system 150 operates with an OCT-scanning beam having the wavelength $\lambda_2$=800 nm. The same reference numerals used in FIGS. 1 and 2 to identify the component groups of the OCT-systems 140 and 150 are used in FIG. 4.

The first scan mirror (144, 154) and the second scan mirror (145, 155) of the OCT-systems (140, 150) are mounted so as to be rotationally moved by position drives (401, 402, 403, 404) about two mutually perpendicularly extending axes (405, 406, 407, 408). This permits the OCT-scanning beams (142, 152) to scan over a plane independently of each other.

The OCT-scanning beam 142 of the first OCT-system 140 is guided to the microscope main objective 101 via the converging lens 147. The OCT-scanning beam 152 of the second OCT-system 150 passes through the microscope main objective 101 via the converging lens 157.

Figure 5:
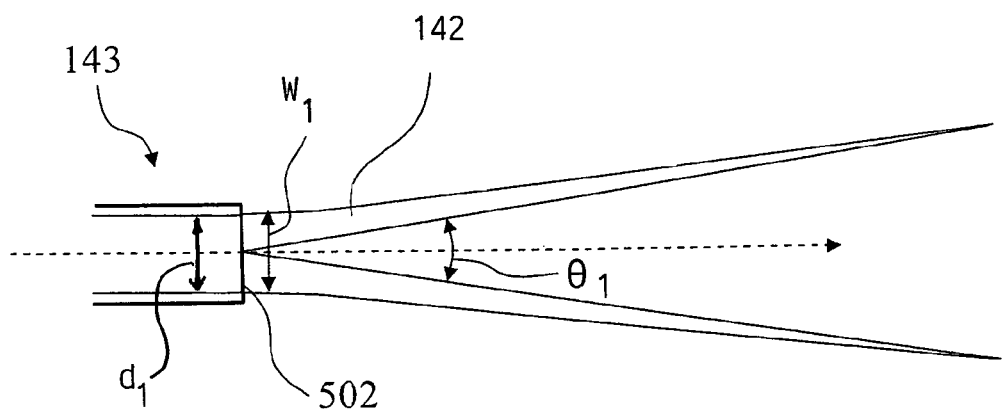
FIG. 5 shows the intensity distribution of the OCT-scanning light beam exiting from the light conductor of the OCT-system in the surgical microscope.

FIG. 5 shows a front portion of the light conductor 143 of FIG. 1 having front face 502. The light conductor 143 operates as a monomode fiber for light of the wavelength $\lambda_1$=1310 nm. The diameter ($d_1$) of the fiber core of the light conductor 143 satisfies the relationship:

$$\frac{d_1}{2} < 2.4 \frac{\lambda_1}{2\pi NA_1},$$

wherein: $NA_1$ is the numerical aperture of the front face of the light conductor. Preferably, the diameter ($d_1$) of the fiber core of the light conductor 143 lies in the range of 5 μm<$d_1$<10 μm. In this parameter range, the light conductor 143 conducts the light with a Gaussian-shaped wave mode. The OCT-scanning light beam 142 exits from the light conductor 143 with an approximately Gaussian-shaped beam profile which is characterized by a waist parameter $W_1$ and an aperture parameter $\theta_1$ wherein:

$$\theta_1 = \frac{\lambda_1}{\pi W_1}$$

An aperture angle of $\theta_1 \approx 0.0827$ rad results thereby as an index for the beam divergence for a fiber core diameter of $d_1=10$ µm and a wavelength $\lambda_1=1310$ nm.

The front face 502 of the light conductor 143 is imaged into an OCT-scanning plane via the following: the scan mirrors 144 and 145 in the surgical microscope 100 of FIG. 1; the converging lens 147; and, the microscope main objective.

Figure 6:
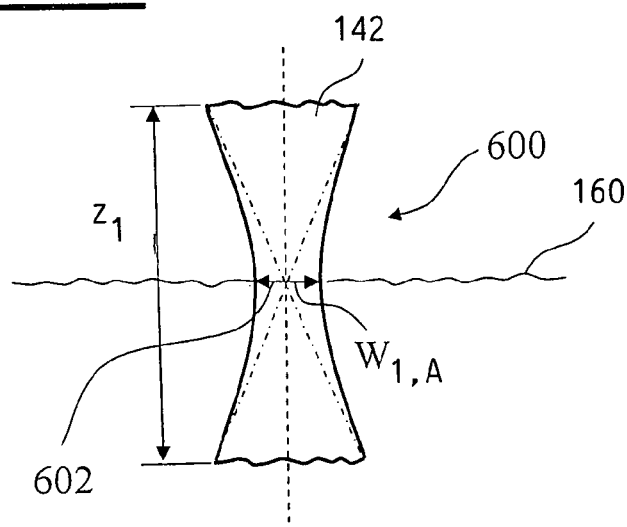
FIG. 6 shows the intensity distribution of the OCT-scanning light beam in the OCT-scanning plane in the object region of the surgical microscope; and, FIGS. 7 and 8 show a modified embodiment for the OCT-system in the surgical microscope.

FIG. 6 shows the course of the intensity distribution of the OCT-scanning light beam 142 perpendicular to the OCT-scanning plane 160. In the OCT scanning plane 160, the intensity distribution of the OCT-scanning radiation has a smallest constriction. The diameter of the OCT-scanning beam path increases outside of the OCT-scanning plane. The OCT-scanning light beam 142 exits from the light conductor 143 of FIG. 5 with an approximately Gaussian-shaped beam profile. For this reason, the converging lens 147 and the microscope main objective 101 of the surgical microscope 100 of FIG. 1 effect a so-called Gaussian bundle 600 of the OCT-scanning light beam 142 for the OCT-scanning beam in the region of the OCT-scanning plane 160. This Gaussian bundle 600 is characterized by the confocal parameter ($z_1$) as an index for the longitudinal expansion of the constriction of the Gaussian bundle and by the waist parameter $W_{1,A}$ as an index for the diameter of the smallest constriction 602 of the OCT-scanning light beam 142 in the OCT-scanning light plane, that is, for the diameter of the constriction thereof. The following applies:

$$z_1 = 2\frac{W_{1,A}^2 \pi}{\lambda_1},$$

wherein: $\lambda_1$ is the wavelength of the OCT-scanning light beam. The following relationship applies between the waist parameter $W_{1,A}$ of the Gaussian bundle 600 and the waist parameter $W_1$ of the scanning light beam 142 (FIG. 5) which exits from the light conductor 143:

$$W_{1,A} = \beta_1 W_1,$$

wherein: $\beta_1$ is the magnification parameter or demagnification parameter of the above-mentioned geometric image of the exit end of light conductor 143 of FIG. 1 in the OCT-scanning plane. The parameter $\beta_1$ is coupled to the focal length $f_{147}$ of the converging lens 147 of FIG. 1 and the focal length $f_2$ of the main objective via the following relationship:

$$\frac{f_2}{f_{147}} = \beta_1$$

The size of structures, which can be resolved with the OCT-scanning light beam 142, is determined by the diameter of the beam 142 in the OCT-scanning plane 160, that is, by the waist parameter $W_1$. If, for example, an application requires a lateral resolution of the OCT-system in the surgical microscope of approximately 40 µm, then, according to the Nyquist theorem, the cross section of the OCT-scanning light beam 142 must amount to approximately 20 µm in the OCT-scanning plane. For a given wavelength $\lambda_1$ for the OCT-scanning light beam 142 of FIG. 1, the magnification of the optical image in the OCT-beam path and the diameter of the fiber core in the light conductor 143 must be suitably selected for a desired resolution of the OCT-system 140.

The confocal parameter ($z_1$) as an index for the longitudinal expansion of the waist of the Gaussian bundle determines the axial depth of field from which backscattered light can be detected in the OCT-scanning beam 142 of FIG. 1. The smaller the confocal parameter ($z_1$), the greater is the loss of the OCT-system with respect to lateral resolution when removing an object from the OCT-scanning plane 160 with this object having been scanned with the OCT-scanning beam. The reason for this is that the location of the scatter centers can be localized only within the "funnel" defined by the waist parameter $W_1$ and the confocal parameter ($z_1$).

As the axial resolution of an OCT-system is delimited on the one hand by the specific coherence length of the light of the light source utilized in the OCT-system and, on the other hand, the lateral resolution of the OCT-system decreases when the depth index thereof exceeds the expansion given by the confocal parameter ($z_1$), the adjustment of the confocal parameter ($z_1$) to the specific coherence length of the light source utilized in the OCT-system is favorable.

For a specific wavelength $\lambda_1$ of the OCT-scanning light beam 142, the possible lateral resolution of the OCT-system of FIG. 1 results because the wavelength $\lambda_1$ and confocal parameter ($z_1$) determine the waist parameter $W_{1,A}$. The optical units in the OCT-scanning beam path of FIG. 1 and the dimensioning of the fiber core of the light conductor 143 are then to be selected so that the particular waist parameter results.

The converging lens 147 in the surgical microscope 100 is preferably so adjusted that the focal plane 170 of the microscope main objective 101 for the visible spectral range and the OCT-scanning plane 160 of the OCT-system 140 are coincident. Then, the waist 502 (FIG. 5) of the OCT-scanning beam lies in the focal plane 170 of the surgical microscope.

For the OCT-scanning beam 152 of the OCT-system 150 of FIG. 2, the light conductor 153 functions as a monomode fiber for light of the wavelength $\lambda_2=800$ nm. The diameter ($d_2$) of the fiber core of the light conductor 153 therefore satisfies the relationship:

$$\frac{d_2}{2} < 2.4 \frac{\lambda_2}{2\pi NA_2}$$

wherein $NA_2$ is the numerical aperture of the front face of the light conductor 153. The OCT-scanning light beam 152 exits from the light conductor 153 with an approximately Gaussian-shaped beam profile which is characterized by a waist $W_2$ and an aperture parameter $\theta_2$ wherein:

$$\theta_2 = \frac{\lambda_2}{\pi W_2}$$

For the waist parameter of the OCT-scanning beam 152 in the OCT-scanning plane 160, the following applies:

$$W_{2,A} = \beta_2 W_2,$$

wherein $\beta_2$ is the demagnification parameter of the geometric image of the exit end of the light conductor 153 of FIG. 2 in the OCT-scanning plane 160.

The parameter $\beta_2$ is defined by the focal length of the converging lens 157 of FIG. 2, the focal length of the microscope main objective 101 as well as by the reducer lens 131, the ophthalmoscopic magnifier lens 132 and the cornea and lens of the patient eye 108.

The converging lens 157 is preferably so adjusted that, when the optical viewing beam images the ocular fundus 190 of the patient eye 108 through the microscope main objective 101, the OCT-scanning plane 160 for the OCT-system 150 in the surgical microscope 100 is coincident with the ocular fundus 190.

Alternatively to the described design of the OCT-systems in the surgical microscope, an offset of the OCT-scanning plane and focal plane can also be provided in the surgical microscope. Preferably, this offset is not greater than the confocal parameter ($z_1$) of the OCT-scanning light beam in the region of the OCT-scanning plane.

In that the OCT-scanning plane is disposed further from the microscope main objective 101 of FIG. 1 by the confocal parameter ($z_1$), the depth measurement index for the OCT-system can be maximized in the object region.

Figure 7:
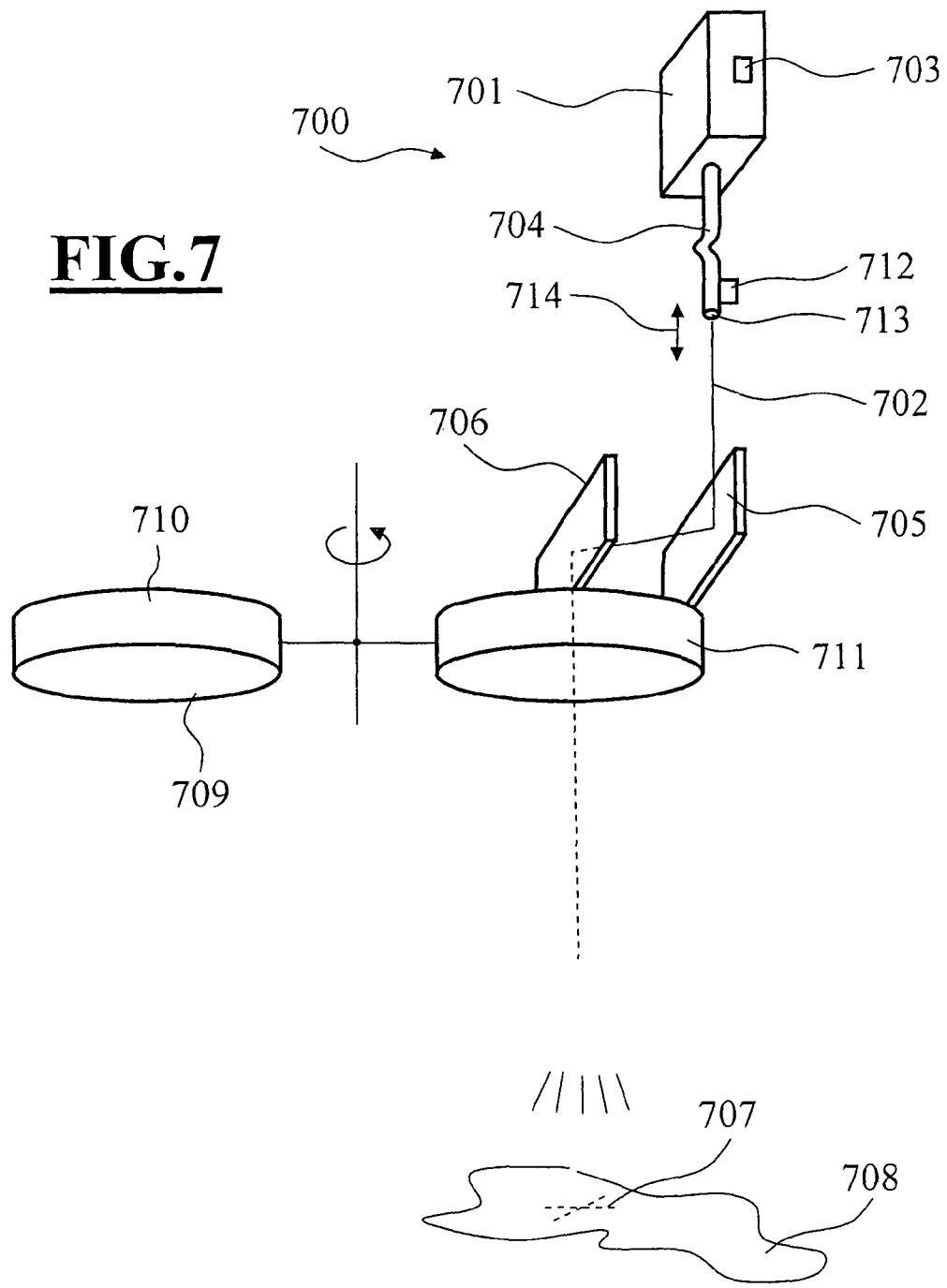

In FIG. 7, a modified embodiment for an OCT-system is shown which can be utilized in the ophthalmic surgical microscope 100 of FIGS. 1 and 2.

Corresponding to the OCT-system 140 of FIG. 1, the OCT-system 700 includes a unit 701 for generating and analyzing an OCT-scanning beam 702. The unit 701 is so designed that OCT-scanning beams having different wavelengths can be generated and evaluated. A control apparatus 703 is provided for adjusting the wavelength of the OCT-system 700.

The OCT-scanning beam 702 exits from a light conductor 704 which is connected to the unit 701. The OCT-scanning beam 702 reaches two scan mirrors (705, 706) which are movable in such a manner by drives (not shown) that an object region 708 can be scanned in an OCT-scanning plane 707.

For the adjustment of different OCT-scanning planes, on the one hand, a magnification exchanger 709 is provided as a lens exchange unit in the OCT-system 700 and this exchanger 709 holds converging lenses of different refractive power (710, 711). These converging lenses (710, 711) can be pivoted into and out of the OCT-scanning beam path 702. In addition, a drive unit 712 is assigned to the light conductor 704 which permits the exit end 713 of the light conductor to be moved in correspondence to the double arrow 714 in order to vary the position of the OCT-scanning plane 707 in the object region.

The OCT-scanning beam 702 reaches the OCT-scanning plane via the converging lens 711 which bundles the scanning rays and conducts the same to the microscope main objective of the corresponding surgical microscope.

Figure 8:
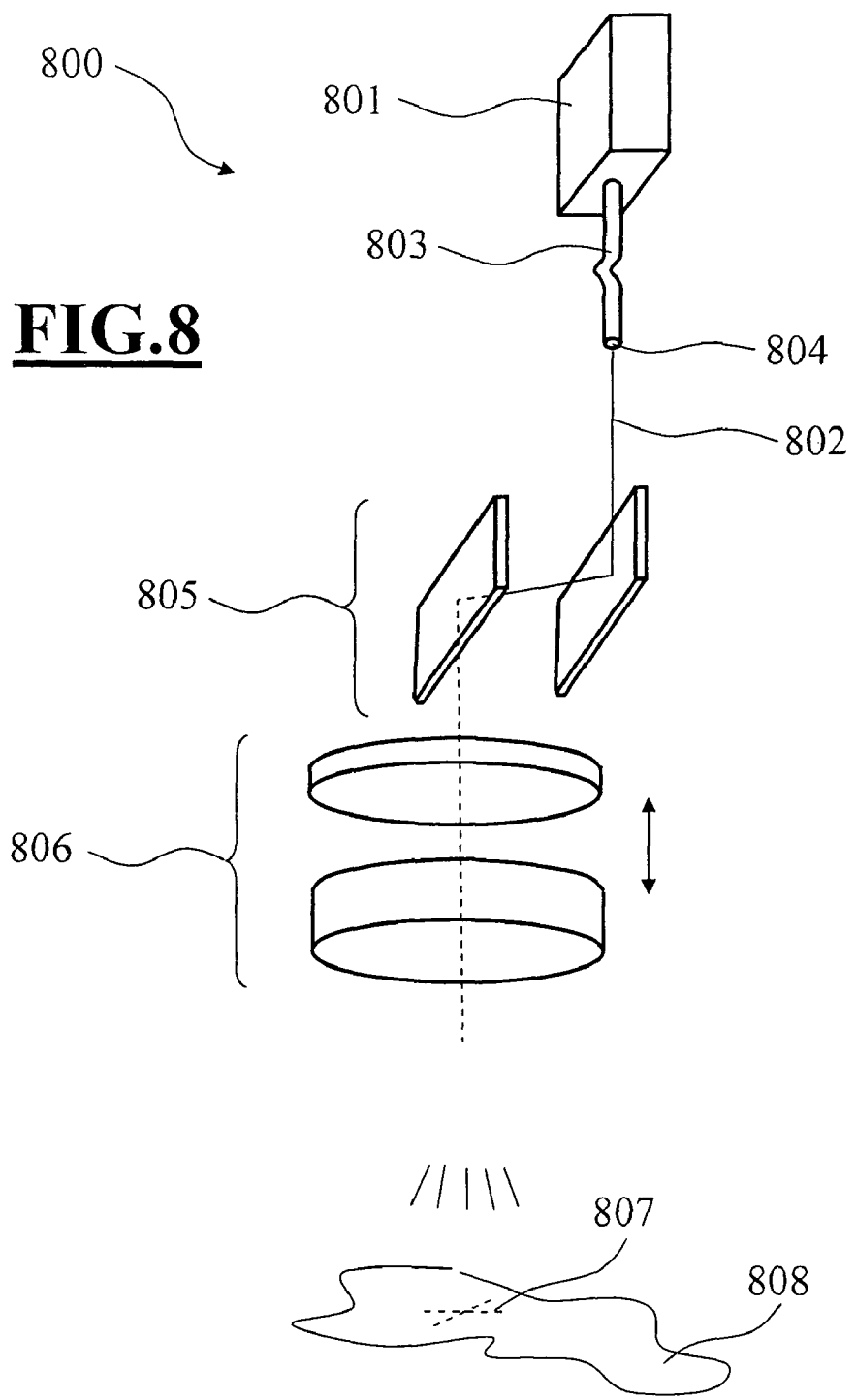

FIG. 8 shows a further embodiment of an OCT-system for an ophthalmic surgical microscope. In the same manner as the OCT-system 700, the OCT-system here has a unit 801 for generating and analyzing an OCT-scanning beam 802 which exits from a light conductor 803. In the OCT-system 800, the OCT-scanning beam 802, which exits from the light conductor exit end 804, is guided by a corresponding scanning mirror system 805 through a lens unit 806 with adjustable refractive power which acts as a zoom system. Accordingly, it is in turn possible to vary the position of the OCT-scanning plane 807 in an object region 808.

A further modified embodiment of the surgical microscope 100 shown in FIG. 1 contains a focusable microscope main objective having an adjustable focal length. This measure too makes it possible to shift an OCT-scanning plane and to change the geometric imaging of the light conductor exit end in the OCT-scanning plane.

It is understood that the foregoing description is that of the preferred embodiments of the invention and that various changes and modifications may be made thereto without departing from the spirit and scope of the invention as defined in the appended claims.

What is claimed is:

1. An ophthalmic surgical microscope for viewing the ocular fundus of the eye of a patient, the ophthalmic surgical microscope defining a viewing beam path and comprising:
    a microscope main objective and an optical assembly including an opthalmoscopic magnifier lens mounted so as to permit said viewing beam path to pass therethrough permitting examination of the ocular fundus;
    an OCT-system for recording images of said ocular fundus;
    said OCT-system providing an OCT-scanning beam and including a scanning mirror device for scanning said OCT-scanning beam;
    said optical assembly being arranged between said main objective and the ocular fundus for passing said viewing beam and said OCT-scanning beam toward the ocular fundus;
    said main objective and said optical assembly conjointly defining a microscope focal plane of said surgical microscope at the ocular fundus; and,
    a focusing device for focusing said OCT-scanning beam onto an OCT-scanning plane so as to provide an offset between said microscope focal plane and said OCT-scanning plane.

2. The ophthalmic surgical microscope of claim 1, wherein said OCT-system comprises generating means for supplying said OCT-scanning beam at a first wavelength and at a second wavelength different from said first wavelength.

3. The ophthalmic surgical microscope of claim 1, wherein said OCT-system is a first OCT-system providing a first OCT-scanning beam and said surgical microscope further comprises a second OCT-system providing a second OCT-scanning beam; and, said first OCT-scanning beam has a first wavelength and said second OCT-scanning beam has a second wavelength different from said first wavelength.

4. The ophthalmic surgical microscope of claim 1, wherein said focusing device includes an optical unit mounted between said scanning mirror device and said microscope main objective for bundling the OCT-scanning beam exiting from said scanning mirror device and guiding the bundled OCT-scanning beam into a beam path passing through said microscope main objective to said ocular fundus.

5. The ophthalmic surgical microscope of claim 4, wherein said optical unit is a movable lens assembly.

6. The ophthalmic surgical microscope of claim 4, further comprising a lens changing unit and said optical unit being mounted in said lens changing unit.

7. The ophthalmic surgical microscope of claim 4, wherein said optical unit is a zoom assembly having a variable focal length.

8. The ophthalmic surgical microscope of claim 4, said surgical microscope further comprising a focal length changing unit for changing the focal length of said microscope main objective.

9. The ophthalmic surgical microscope of claim 4, wherein said scanning mirror device includes a first scanning mirror; and, a first device for rotating said first scanning mirror about a first rotational axis.

10. The ophthalmic surgical microscope of claim 9, wherein said scanning mirror device comprises a second scanning mirror; and, a second device for rotating said second mirror about a second rotational axis laterally offset at right angles to said first rotational axis.

11. The ophthalmic surgical microscope of claim 4, wherein said OCT-system further comprises a light conductor having an end portion having a light exit end face for said OCT-scanning beam; and, means for moving said end portion.

12. The ophthalmic surgical microscope of claim 1, said optical assembly further comprising a reduction lens disposed between said microscope main objective and said opthalmoscopic magnifier lens.

13. The ophthalmic surgical microscope of claim 1, wherein said OCT-scanning beam has an intensity distribution defined as a Gaussian bundle wherein the intensity distribution of the OCT-scanning radiation has a smallest constriction in the OCT-scanning plane and wherein said Gaussian bundle is characterized by a confocal parameter ($z_1$) as an index for the longitudinal expansion of the constriction of said Gaussian bundle measured along the longitudinal axis of said OCT-scanning beam; and, said focusing device is adjustable so as to cause said offset not to exceed said confocal parameter ($z_1$).

14. The ophthalmic surgical microscope of claim 13, wherein said focusing device comprises: a converging lens for focusing said OCT-scanning beam onto said ocular fundus; and, a displacing mechanism for displacing said converging lens to effect said focusing of said OCT-scanning beam so as to permit the position of said OCT-scanning plane to be adjusted independently of said microscope focal plane.

15. The ophthalmic surgical microscope of claim 1, said opthalmoscopic magnifier lens being movable between a first position whereat said viewing beam path and said OCT-scanning beam path pass through said opthalmoscopic magnifier lens and a second position whereat said viewing beam path and said OCT-scanning beam path do not pass through said opthalmoscopic magnifier lens.

16. The ophthalmic surgical microscope of claim 15, wherein said OCT-system defines a reference beam path; and, said surgical microscope further comprises a coupling device for increasing the optical path length of said reference beam path by a given value when moving said opthalmoscopic magnifier lens into said first position.

17. The ophthalmic surgical microscope of claim 15, further comprising a reduction lens being movably mounted; said reduction lens being movable into a first position whereat said viewing beam path and said OCT-scanning beam pass through said reduction lens, and into a second position whereat said viewing beam path and said OCT-scanning beam do not pass through said reduction lens.

18. The ophthalmic surgical microscope of claim 15, further comprising an ancillary module being movably mounted; said ancillary module having an optical assembly including at least one of said opthalmoscopic magnifier lens and a reduction lens; and, said ancillary module being movable between a first position whereat said viewing beam path and said OCT-scanning beam pass through said optical assembly and a second position whereat said viewing beam path and said OCT-scanning beam do not pass through said optical assembly.

* * * * *

UNITED STATES PATENT AND TRADEMARK OFFICE
CERTIFICATE OF CORRECTION

| | | |
|---|---|---|
| PATENT NO. | : 7,839,494 B2 | Page 1 of 1 |
| APPLICATION NO. | : 11/984819 | |
| DATED | : November 23, 2010 | |
| INVENTOR(S) | : Reimer et al. | |

It is certified that error appears in the above-identified patent and that said Letters Patent is hereby corrected as shown below:

On Title Page:
Item (30) Foreign Application Priority Data: delete "Nov. 6, 2006 (DE) ............ 10 2006 052 513".

Column 1:
Line 9: delete "which are".

Column 2:
Line 61: delete "rapid-back" and substitute -- rapid back -- therefor.

Signed and Sealed this
Fourteenth Day of June, 2011

David J. Kappos
*Director of the United States Patent and Trademark Office*